(12) United States Patent
Lafontaine

(10) Patent No.: US 6,520,939 B2
(45) Date of Patent: Feb. 18, 2003

(54) HEMOSTASIS VALVE

(75) Inventor: Daniel M. Lafontaine, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 39 days.

(21) Appl. No.: 09/782,764

(22) Filed: Feb. 13, 2001

(65) Prior Publication Data

US 2002/0111585 A1 Aug. 15, 2002

(51) Int. Cl.⁷ .................................................. A61M 5/31
(52) U.S. Cl. .................................. 604/167.03; 604/256
(58) Field of Search ............................. 604/167.03, 256

(56) References Cited

U.S. PATENT DOCUMENTS

| | | | |
|---|---|---|---|
| 4,000,739 A | 1/1977 | Stevens | 128/214.4 |
| 4,254,773 A | 3/1981 | Waldbillig | 128/348 |
| 4,366,817 A | 1/1983 | Thomas | 604/174 |
| 4,424,833 A | 1/1984 | Spector et al. | 137/849 |
| 4,430,081 A | 2/1984 | Timmermans | 604/256 |
| 4,436,519 A | 3/1984 | O'Neill | 604/175 |
| 4,798,594 A | 1/1989 | Hillstead | 604/167 |
| 4,874,378 A | 10/1989 | Hillstead | 604/167 |
| 4,895,565 A | 1/1990 | Hillstead | 604/167 |
| 4,909,798 A | 3/1990 | Fleischhacker et al. | 604/256 |
| 4,929,235 A | 5/1990 | Merry et al. | 604/167 |
| 4,944,729 A | 7/1990 | Buckberg et al. | 604/164 |
| 4,946,133 A | 8/1990 | Johnson et al. | 251/149.1 |
| 4,950,257 A | 8/1990 | Hibbs et al. | 604/265 |
| 4,960,412 A | 10/1990 | Fink | |
| 5,000,745 A | 3/1991 | Guest et al. | 604/256 |
| 5,045,065 A | 9/1991 | Raulerson | 604/167 |
| 5,059,186 A | 10/1991 | Yamamoto et al. | 604/280 |
| 5,092,857 A | 3/1992 | Fleischhacker | 604/256 |
| 5,098,393 A | 3/1992 | Amplatz et al. | 604/167 |
| 5,114,408 A | 5/1992 | Fleischhaker et al. | 604/167 |
| 5,137,519 A | 8/1992 | Littrell et al. | 604/174 |
| 5,154,701 A | 10/1992 | Cheer et al. | 604/167 |

(List continued on next page.)

FOREIGN PATENT DOCUMENTS

| | | |
|---|---|---|
| EP | 0 344 907 A2 | 12/1989 |
| EP | 0 369 314 A2 | 5/1990 |
| EP | 0 442 194 A2 | 6/1991 |
| EP | 0 692 278 A1 | 1/1996 |
| WO | WO 99/06099 | 2/1999 |
| WO | WO 99/34849 | 7/1999 |

OTHER PUBLICATIONS

US 5,520,663, 5/1996, Patterson et al. (withdrawn)

Product Brochure: Pinnacle® Introducer Sheaths, undated, 3 sheets.

*Primary Examiner*—Philippe Derakshani
(74) *Attorney, Agent, or Firm*—Crompton, Seager & Tufte, LLC

(57) ABSTRACT

A hemostasis valve which provides a fluid tight seal at all times to prevent back-bleeding, and offers relatively low friction when devices are inserted therein. The hemostasis valve may either be an integral part of a tubular device (e.g., sheath, catheter, or the like) or releasable from the tubular device (e.g., Y-adapter or the like). In one embodiment, the hemostasis valve is biased to a closed position in response to distal pressure to prevent back-bleeding. The hemostasis valve is also biased to an open position in response to proximal force or pressure to reduce friction when devices are inserted therein. For example, the hemostasis valve may comprise a plurality of leaflets or flaps. In another embodiment, the hemostasis valve is longitudinally actuated between an open position to reduce friction during device insertion and a closed position to prevent back-bleeding when no devices are inserted therein.

20 Claims, 3 Drawing Sheets

U.S. PATENT DOCUMENTS

| | | |
|---|---|---|
| 5,167,637 A | 12/1992 | Okada et al. ............... 604/167 |
| 5,188,607 A | 2/1993 | Wu ........................... 604/167 |
| 5,234,410 A | 8/1993 | Graham et al. ............ 604/167 |
| 5,242,410 A | 9/1993 | Melker ....................... 604/164 |
| 5,242,413 A | 9/1993 | Heiliger .................... 604/167 |
| 5,267,966 A | 12/1993 | Paul .......................... 604/167 |
| 5,269,763 A | 12/1993 | Boehmer et al. |
| 5,295,657 A | 3/1994 | Atkinson ................ 251/149.1 |
| 5,300,033 A | 4/1994 | Miller ....................... 604/167 |
| 5,330,435 A | 7/1994 | Vaillancourt ............... 604/167 |
| 5,350,363 A | 9/1994 | Goode et al. .............. 604/167 |
| 5,402,982 A | 4/1995 | Atkinson et al. ........ 251/149.1 |
| 5,453,095 A | 9/1995 | Davila et al. .............. 604/167 |
| 5,499,975 A | 3/1996 | Cope et al. ................. 604/165 |
| 5,520,655 A | 5/1996 | Davila et al. .............. 604/167 |
| 5,538,505 A | 7/1996 | Weinstein et al. .......... 604/167 |
| 5,549,576 A | 8/1996 | Patterson et al. ........... 604/247 |
| 5,613,956 A | 3/1997 | Patterson et al. ........... 604/256 |
| 5,693,025 A * | 12/1997 | Stevens ................ 604/167.03 |
| 5,752,970 A | 5/1998 | Yoon |
| 5,762,630 A | 6/1998 | Bley et al. ................. 604/164 |
| 5,807,350 A | 9/1998 | Diaz ......................... 604/256 |
| 5,843,031 A | 12/1998 | Hermann et al. ............. 604/95 |
| 5,911,710 A | 6/1999 | Barry et al. ................ 604/249 |
| 5,944,697 A | 8/1999 | Biche ........................ 604/174 |
| 6,287,280 B1 * | 11/2001 | Lampropoulos et al. .... 604/256 |

* cited by examiner

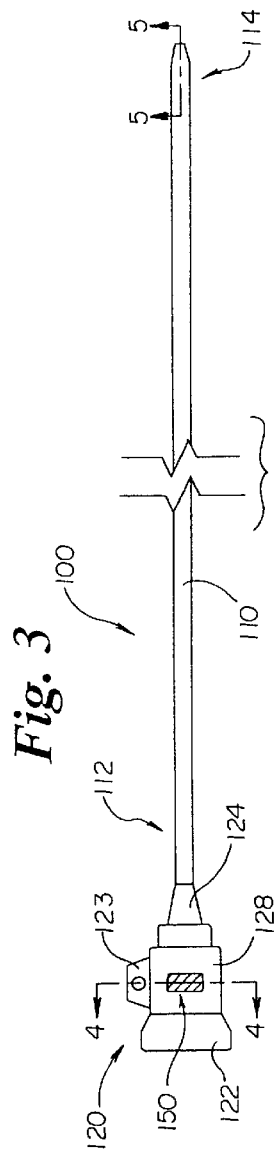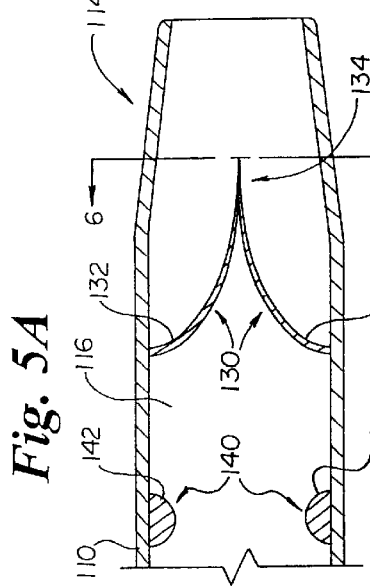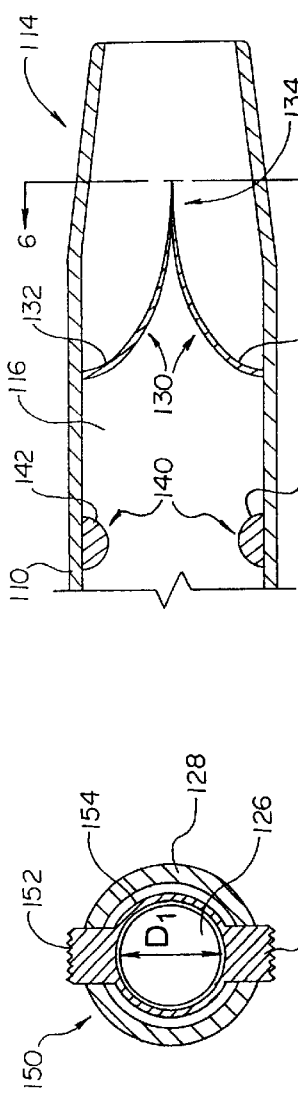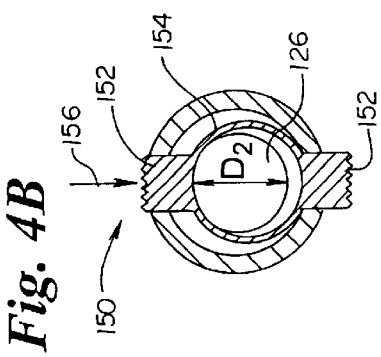

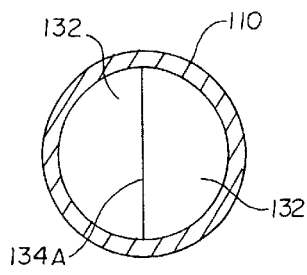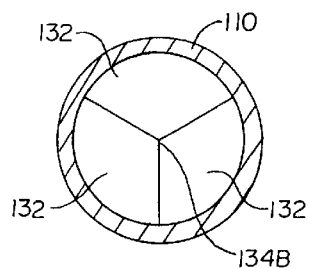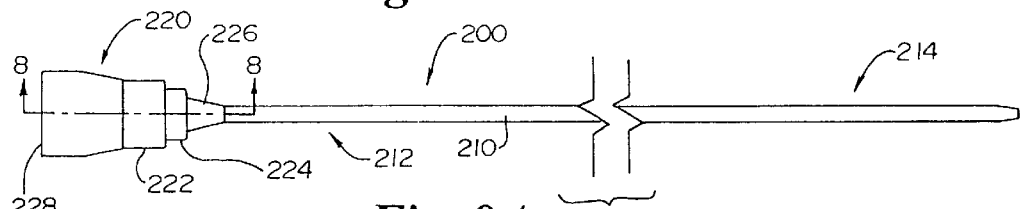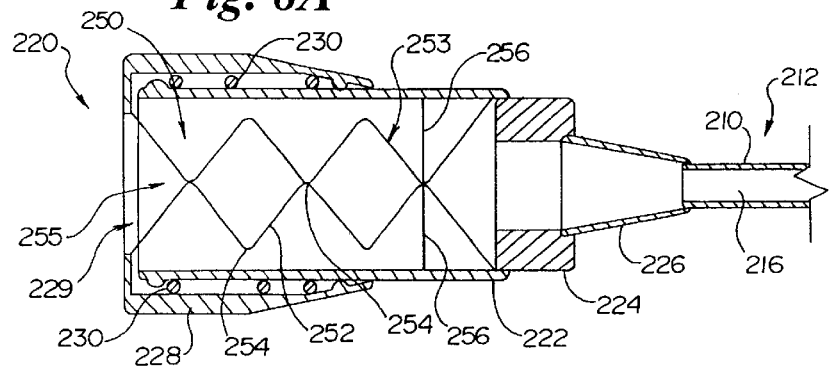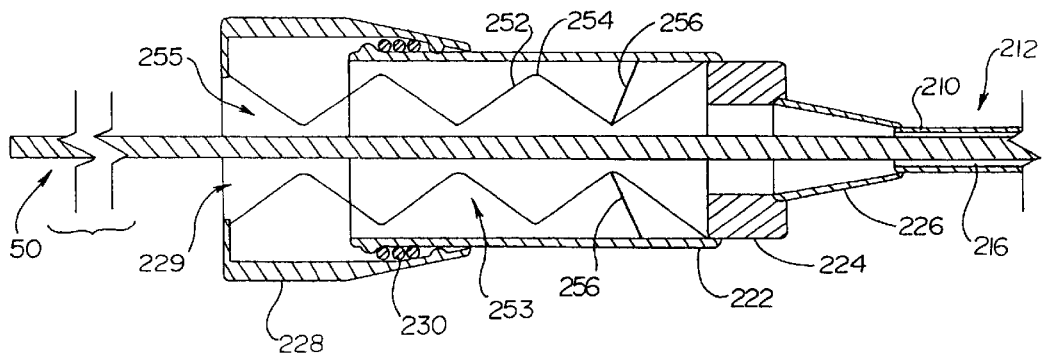

HEMOSTASIS VALVE

FIELD OF THE INVENTION

The present invention generally relates to devices incorporating hemostasis valves. More specifically, the present invention relates to hemostasis valves for use with vascular introducer sheaths, catheters, Y-adapters and the like.

BACKGROUND OF THE INVENTION

Vascular introducer sheaths are well known components of vascular access systems which are used in a wide variety of diagnostic and therapeutic vascular procedures, such as angiography, angioplasty and embolization procedures. Vascular access systems typically include an introducer sheath and a dilator. The introducer sheath usually includes a hemostasis valve which inhibits blood loss as guide wires, catheters and the like are introduced, passed through and manipulated in the sheath.

An example of a conventional vascular access system 10 is illustrated in FIG. 1. The vascular access system 10 includes two primary components, namely an introducer sheath 12 and a dilator 14. The introducer sheath 12 includes an elongate shaft 16 and a hemostasis valve assembly 18. A flush tube subassembly 20 may be connected to a side port 22 of the hemostasis assembly 18. Although not clearly visible, the hemostasis valve assembly 18 includes a hub, a cap and a gasket 30 (shown in FIGS. 2A and 2B) disposed therebetween.

The gasket 30 of the hemostasis valve assembly 18 forms a fluid seal about devices inserted therein to inhibit back-bleeding. The gasket 30 may comprise a disc of flexible polymeric material having a slit 32 extending therethrough as shown in FIG. 2A or a hole 34 as shown in FIG. 2B. The slit 32 is sufficiently flexible and the hole 34 is sufficiently sized to form a seal about devices inserted therein. The slit 32 is normally closed such that a hemostatic seal is formed with or without devices inserted therein. By contrast, the hole 34 is normally open such that a hemostatic seal is formed only with a device inserted therein.

An advantage of the slit 32 design is that back-bleeding is prevented at all times—prior to, during and subsequent to device insertion. A disadvantage of the slit 32 design is that a significant amount of friction may be encountered when sliding devices therethrough. An advantage of the hole 34 design is that relatively little friction is encountered when sliding devices therethrough. A disadvantage of the hole 34 design is that back-bleeding may occur when no device is inserted therein (i.e., prior to and subsequent to device insertion). Accordingly, there is a need for a hemostasis valve which provides a fluid tight seal at all times to prevent back-bleeding, and offers relatively low friction when devices are inserted therein.

SUMMARY OF THE INVENTION

To address this need, the present invention provides an improved hemostasis valve for use with an intravascular device such as an introducer sheath, a catheter or the like. In all embodiments, the hemostasis valve may either be an integral part of the device, or releasable from the device as in a Y-adapter, a manifold or the like.

In one embodiment, the hemostasis valve is normally closed and is biased to a closed position in response to distal pressure to prevent back-bleeding. The hemostasis valve is also biased to an open position in response to proximal force or pressure to reduce friction when devices are inserted therein. For example, the hemostasis valve may comprise a plurality of flaps or leaflets, such as a bileaflet or trileaflet design. Preferably, the leaflets are cuspidate, such as a bicuspid or tricuspid design. Also preferably, the thickness of the leaflets is substantially less than the radial dimension thereof such that the leaflets readily deflect and conform. As an alternative, another hemostasis valve (e.g., a close-fit seal) may be utilized to ensure a fluid tight seal about devices inserted therein.

In another embodiment, the hemostasis valve is longitudinally actuated between an open position to reduce friction during device insertion and a closed position to prevent back-bleeding when no devices are inserted therein. The hemostasis valve may include a circular or helical pleat which changes in radial dimension upon longitudinal actuation. For example, the hemostasis valve may be bellows-shaped. The hemostasis valve may also include a radial compression member that toggles when the valve is closed to ensure a fluid tight seal.

BRIEF DESCRIPTION OF THE DRAWINGS

FIG. 3 is a plan view of an introducer sheath in accordance with an embodiment of the present invention;

FIG. 4A is a cross-sectional view taken along line 4—4 in FIG. 3, showing the brake mechanism in the disengaged position;

FIG. 4B is a cross-sectional view taken along line 4—4 in FIG. 3 showing the brake mechanism in the engaged position;

FIG. 5A is a longitudinal sectional view taken along line 5—5 in FIG. 3, showing an active and a passive hemostasis valve in accordance with an embodiment of the present invention;

FIG. 5B is a longitudinal sectional view taken along line 5—5 in FIG. 3, showing a tubular catheter extending through the active and passive hemostasis valves illustrated in FIG. 5A;

FIG. 6A is a cross-sectional view taken along line 6—6 in FIG. 5A, showing a bileaflet valve design in accordance with an embodiment of the present invention;

FIG. 6B is a cross-sectional view taken along line 6—6 in FIG. 5A, showing a trileaflet valve design in accordance with an embodiment of the present invention;

FIG. 7 is a plan view of an introducer sheath in accordance with another embodiment of the present invention;

FIG. 8A is a longitudinal sectional view taken along line 8—8 in FIG. 7, showing a hemostasis valve in the closed position; and FIG. 8B is a longitudinal sectional view taken along line 8—8 in FIG. 7, showing the hemostasis valve in the open position with a guide wire extending therethrough.

DETAILED DESCRIPTION OF THE INVENTION

Figure 1:
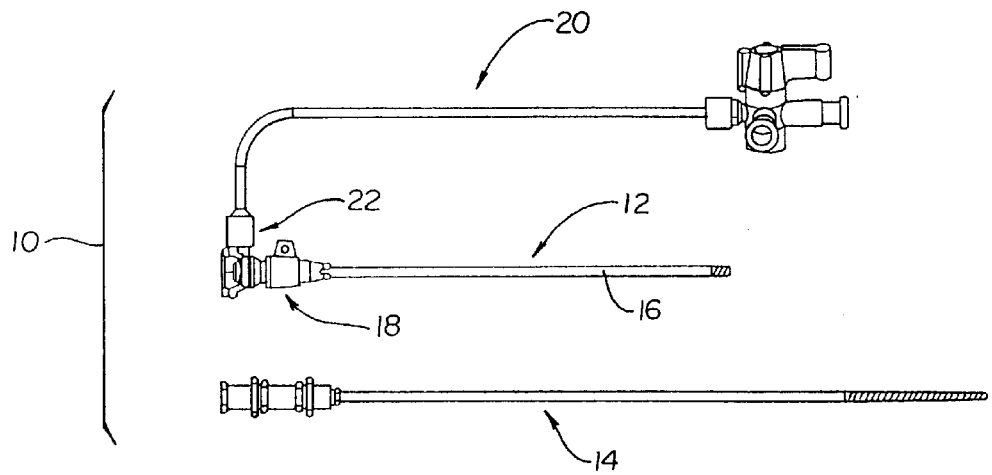
FIG. 1 is a plan view of a conventional vascular access system including an introducer sheath and a dilator.
Figure 2A:
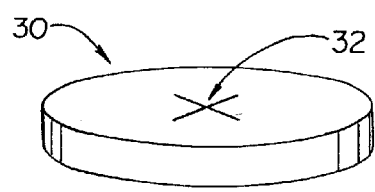
FIG. 2A is a plan view of a conventional slit-type gasket used in the hemostasis valve subassembly of the introducer sheath illustrated in FIG. 1.
Figure 2B:
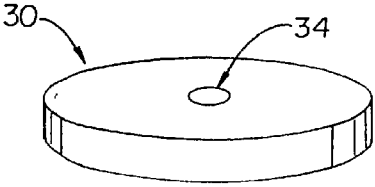
FIG. 2B is a plan view of a hole-type gasket used in the hemostasis valve subassembly of the introducer sheath illustrated in FIG. 1.

The following detailed description should be read with reference to the drawings in which similar elements in different drawings are numbered the same. The drawings, which are not necessarily to scale, depict illustrative embodiments and are not intended to limit the scope of the invention.

Refer now to FIG. 3 which illustrates a side view of an introducer sheath 100 in accordance with an embodiment of the present invention. The introducer sheath 100 includes an elongate shaft 110 having a proximal portion 112, a distal portion 114 and a lumen 116 extending therethrough. A hub assembly 120 is connected to the proximal portion 112 of the shaft 110. A tapered distal tip is connected to the distal portion 114 of the elongate shaft 110 to facilitate smooth insertion into the vascular system. The introducer sheath 100, with the exception of the hub assembly 120 and hemostasis valves 130/140 (discussed hereinafter), may have conventional dimensions and may be formed of conventional materials known in the art. For example, the shaft 110 may have a size ranging from 4F to 14F and a length ranging from 10 cm to 25 cm, and may comprise a tubular polymeric extrusion.

The hub assembly 120 includes a housing or body portion 128 which contains a brake mechanism 150 (discussed hereinafter). The housing or body portion 128 includes a proximal flared portion 122 and a distal strain relief 124. The flared proximal portion 122 includes a proximal opening (not visible) leading to a lumen 126 extending through the hub assembly 120. The strain relief 124 facilitates a kink-resistant connection to the proximal portion 112 of the shaft 110. With this arrangement, other intravascular devices (e.g., tubular catheters 40, guide wires 50, etc) may be inserted into the opening of the flared proximal portion 122, through the lumen 126 of the hub 120, through the lumen 116 of the shaft 110, and into the patient's vascular system. A suture ring 123 may be connected to the housing 128 to secure the introducer sheath 110 to the patient.

The brake mechanism 150 is slidably disposed in the housing 128 of the hub assembly 120 between a disengaged position as shown in FIG. 4A and an engaged position as illustrated in FIG. 4B. In the engaged position, the brake mechanism 150 limits relative longitudinal movement between the introducer sheath 100 and devices inserted therein. Those skilled in the art will recognize that many alternative mechanisms may be used in place of brake mechanism 150 to perform the same or similar function.

The brake mechanism 150 includes opposing buttons 152 which are slidably disposed in similarly shaped openings (not visible) defined in the housing 128. The brake mechanism 150 also includes a collar 154 having an inside diameter approximately equal to the inside diameter of the hub lumen 126, which is approximately equal to the inside diameter of the shaft lumen 116. When the brake mechanism is in the disengaged position as illustrated in FIG. 4A, the lumen of the collar 154 is in alignment with the hub lumen 126 to define a through passage having a nominal diameter $D_1$. When the brake mechanism 150 is in the engaged position as illustrated in FIG. 5B, the lumen of the collar 154 is in misalignment relative to the hub lumen 126 to define a through passage having a reduced diameter $D_2$.

The brake mechanism 150 may be engaged and disengaged by applying a manual force to one of the push buttons 152 as shown, for example, by arrow 156. By engaging the brake mechanism 150, the collar 154 frictionally engages devices extending therethrough by virtue of the reduced diameter $D_2$ and the misalignment with the hub lumen 126. The degree of frictional engagement may be modified, for example, by varying the displacement of the collar 154, and/or by varying the coefficient of friction of the collar 154. Although not shown, the brake mechanism 150 may incorporate a biasing member such as a spring to preferentially bias the brake mechanism 150 to either the engaged position or the disengaged position.

The introducer sheath 100 includes an active hemostasis valve 130 and a passive hemostasis valve 140. The active hemostasis valve 130 and the passive hemostasis valve 140 are adapted to seal about a wide variety of intravascular devices such as a catheter 40 or a guide wire 50. The hemostasis valves 130/140 may be incorporated into a wide variety of intravascular tubular devices such as an introducer sheath, a catheter or the like. The hemostasis valves 130/140 may be incorporated into any portion of the tubular device (e.g., hub or shaft), at a common position or at different positions. In addition, the hemostasis valves 130/140 may be an integral part of the tubular device or releasably connected thereto as with a Y-adapter, a manifold, or the like. For purposes of illustration only, the hemostasis valves 130/140 are shown in FIGS. 5A and 5B to be an integral part of the distal portion 114 of the elongate shaft 110 of the introducer sheath 100, which offers certain advantages.

The active hemostasis valve 130 is normally closed and is biased to a closed position as shown in FIG. 5A in response to distal pressure to minimize back-bleeding when no device extends therethrough. The active hemostasis valve 130 is also preferably biased to an open position in response to proximal force or pressure when devices are inserted therein to reduce friction therebetween.

The active hemostasis valve 130 may comprise a plurality of leaflets or flaps 132. For example, the active hemostasis valve 130 may include two leaflets (bileaflet design) or three leaflets (trileaflet design). Preferably, the leaflets 132 are cuspidate and thereby form a cusp 134. With a bileaflet design as seen in FIG. 6A, the leaflets 132 define a bicuspid interface 134A. With a trileaflet design as shown in FIG. 6B, the leaflets 132 form a tricuspid interface 134B.

In either embodiment, the leaflets 132 preferably have a thickness that is substantially less than the radial dimension thereof such that the leaflets are extremely flexible and readily deflect and conform to devices extending therethrough. For example, the thickness of the leaflets 132 may be 1%–10% of the radial dimension thereof. The leaflets 132 may be formed of a relatively flexible material such as an elastomeric polymeric material (e.g., polyisoprene rubber).

The passive hemostasis valve 140 is normally open to allow devices to freely pass therethrough. The passive hemostasis valve 140 provides a close-fit, relatively low friction, fluid tight seal about devices inserted therein. The passive hemostasis valve 140 may comprise a flexible polymeric O-ring 142 having an inside diameter which is approximately equal to the outside diameter of the intravascular device (e.g., catheter 40) extending therethrough. The inside diameter of the O-ring 142 may be slightly less than the outside diameter of the catheter 40 to create an interference fit which provides a relatively high pressure seal therebetween. Alternatively, the O-ring 142 may have an inside diameter that is slightly greater than the outside diameter of the catheter 40 to define a gap fit which provides a relatively low friction seal therebetween. The passive hemostasis valve 140 ensures a fluid seal about devices inserted therethrough to the extent that the active hemostasis valve 130 does not provide a sufficiently tight seal.

Refer now to FIG. 7 which illustrates a plan view of introducer sheath 200 in accordance with another embodiment of the present invention. The introducer sheath 200 includes an elongate shaft 210 having a proximal portion 212, a distal portion 214 and a lumen 216 extending therethrough. A hub assembly 220 is connected to the proximal portion 212 of the elongate shaft 210. The distal portion 214 of the elongate shaft 210 includes a tapered tip to facilitate insertion into the patient's vascular system. The introducer sheath 200, with the exception of the hub assembly 220, may have conventional dimensions and may be formed of conventional materials known in the art. For example, the shaft 210 may have a size ranging from 4F to 14F and a length ranging from 10 cm to 25 cm, and may comprise a tubular polymeric extrusion.

Hub assembly 220 includes a tubular housing 222 having a proximal end and a distal end. A strain relief 226 is connected to the distal end of the housing 222 by way of connection member 224. The strain relief 226 facilitates a kink-resistant connection to the proximal portion 212 of the shaft 210. The hub assembly 220 further includes a cap 228 which is slidably disposed about the housing 222. The cap 228 includes a proximal opening 229.

The hub assembly 220 further includes an active hemostasis valve 250 having a proximal end and a distal end. The proximal end of the active hemostasis valve 250 is connected the proximal end of the cap 228. The distal end of the active hemostasis valve 250 is connected the distal end of the housing 222. The active hemostasis valve 250 includes a passageway 255 which may be selectively closed as illustrated in FIG. 8A and selectively opened as illustrated in FIG. 8B. A biasing member 230 such as a helical spring may be disposed between the cap 228 and the housing 222 to preferentially basis the hemostasis valve 250 to the closed position or the open position. A lock mechanism (not shown) such as a push-button pin or quarter-turn stop may be used to activate or deactivate the biasing member 230.

The active hemostasis valve 250 includes a plurality of tubular pleats 253 defined by a plurality of wall members 252 connected at circular or helical hinge points 254. For example, the plurality of pleats 253 may resemble a bellows. The active seal 250 may be longitudinally displaced to selectively open and close the passage 255 extending therethrough. The active hemostasis valve 250 may be longitudinally displaced by moving the cap 228 relative to the housing 222. Thus, the passage 255 may be closed by moving the cap 228 in a distal direction relative to the housing 222 as illustrated in FIG. 8A. Similarly, the passage 255 may be opened by displacing the cap 228 in a proximal direction relative to the housing 222 as illustrated in FIG. 8B. In the closed position, the active hemostasis valve 250 prevents back-bleeding through the lumen 216. In the open position, the active hemostasis valve 250 permits insertion of a catheter 40 or a guide wire 50 through the passage 255.

The hemostasis valve 250 may include a radial compression member 256 having an outer perimeter connected to the housing 222 and an inner perimeter connected to the outside surface of a pleat 253 adjacent an inside hinge point 254. The radial compression member 256 toggles to a closed position as illustrated in FIG. 8A to ensure a fluid tight seal and thereby prevent back-bleeding. The radial compression member 256 is radially rigid in the closed position as shown in FIG. 8A and radially flexible in the open position as illustrated in FIG. 8B. The radial compression member 256 may comprise, for example, a thin disk having a central opening disposed about an inside hinge point 254.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular device adapted to accommodate another intravascular device therein, the intravascular device comprising:
   a shaft having a proximal portion, a distal portion and a lumen extending therethrough; and
   a first hemostasis valve connected to the distal portion of the shaft, the first hemostasis valve being biased to an open position in response to proximal pressure and biased to a closed position in response to distal pressure.

2. An intravascular device as in claim 1, wherein the first hemostasis valve is normally closed.

3. An intravascular device as in claim 1, wherein the first hemostasis valve is releasably connected to the shaft.

4. An intravascular device as in claim 1, wherein the first hemostasis valve comprises a plurality of leaflets.

5. An intravascular device as in claim 4, wherein the leaflets are cuspidate.

6. An intravascular device as in claim 5, wherein the leaflets have a radial dimension and a thickness, and wherein the thickness is substantially less than the radial dimension such that the leaflets readily deflect.

7. An intravascular device as in claim 1, further comprising a second hemostasis valve connected to the shaft, the second hemostasis valve being normally open.

8. An intravascular device as in claim 7, wherein the second hemostasis valve is passive.

9. An intravascular device adapted to accommodate another intravascular device therein, the intravascular device comprising:
   a shaft having a proximal portion, a distal portion and a lumen extending therethrough;
   a first hemostasis valve connected to the distal portion of the shaft, the first hemostasis valve being active; and
   a second hemostasis valve connected to the shaft, the second hemostasis valve being passive.

10. An intravascular device as in claim 9, wherein the first hemostasis valve is biased to an open position in response to proximal pressure and is biased to a closed position in response to distal pressure.

11. An intravascular device as in claim 10, wherein the first hemostasis valve comprises a plurality of leaflets.

12. An intravascular device as in claim 11, wherein the first hemostasis valve is normally closed.

13. An intravascular device as in claim 12, wherein the second hemostasis valve is normally open.

14. An intravascular device adapted to accommodate another intravascular device therein, the intravascular device comprising:
   a shaft having a proximal portion, a distal portion and a lumen extending therethrough;
   a hemostasis valve including a helical spring connected to the shaft, the hemostasis valve being longitudinally actuatable between an open position and a closed position.

15. An intravascular device as in claim 14, wherein the hemostasis valve is releasably connected to the shaft.

16. An intravascular device as in claim 14, wherein the hemostasis valve includes a pleat which changes in radial dimension upon longitudinal actuation.

17. An intravascular device as in claim 16, wherein the hemostasis valve is bellows-shaped.

18. An intravascular device as in claim 16, wherein the hemostasis valve includes a toggled compression member.

19. A method of using a hemostasis valve, comprising the steps of:
   providing an intravascular device adapted to accommodate another intravascular device therein, the intravascular device including a shaft having a proximal portion, a distal portion and a lumen extending therethrough;
   providing a hemostasis valve having a helical spring connected to the shaft; and
   longitudinally actuating the hemostasis valve between an open position and a closed position.

20. A method of using a hemostasis valve as in claim 19, wherein the hemostasis valve is releasably connected to the shaft, further comprising the step of connecting the hemostasis valve to the shaft.

* * * * *